United States Patent [19]

Tanaka et al.

[11] Patent Number: 4,920,973
[45] Date of Patent: May 1, 1990

[54] SKIN TEMPERATURE MEASURING APPARATUS FOR DIAGNOSING DISTURBANCE OF PERIPHERAL CIRCULATION

[75] Inventors: Isamu Tanaka, Fukuoka; Fuminao Tanitomi, Ueki, both of Japan

[73] Assignee: Kaisei Koguy Corporation, Kumamoto, Japan

[21] Appl. No.: 164,929

[22] Filed: Mar. 7, 1988

[30] Foreign Application Priority Data

Apr. 17, 1987 [JP] Japan .................................. 62-94840

[51] Int. Cl.$^5$ .............................................. A61B 5/00
[52] U.S. Cl. .................................................... 128/736
[58] Field of Search ........ 128/736, 760, 734, 399–402, 128/633, 634; 374/166, 31, 100–103, 112, 124, 137, 142, 109, 141; 604/113, 291

[56] References Cited

U.S. PATENT DOCUMENTS

| | | | |
|---|---|---|---|
| 4,175,543 | 11/1979 | Suzuki et al. | 128/736 |
| 4,175,567 | 11/1979 | Patel | 128/736 |
| 4,343,854 | 9/1982 | Gosline | 128/736 X |
| 4,386,604 | 6/1983 | Heshey | 128/736 |
| 4,399,823 | 8/1983 | Donnelly | 128/736 |
| 4,502,487 | 3/1985 | DuBrucq et al. | 128/736 X |
| 4,572,213 | 2/1986 | Kawahara | 128/736 |
| 4,576,182 | 3/1986 | Normann | 128/736 X |
| 4,626,110 | 12/1986 | Wickersheim et al. | 128/736 X |
| 4,662,360 | 5/1987 | O'Hara et al. | 128/736 X |

*Primary Examiner*—Max Hindenburg
*Assistant Examiner*—John P. Lacyk
*Attorney, Agent, or Firm*—Townsend & Townsend

[57] ABSTRACT

A skin temperature measuring apparatus for diagonising disturbance of peripheral circulation of a patient having a cold air box including a thermo regulator of low temperature. A radiation thermometer is disposed in the cold air box for measuring the skin temperature of a test section of the patient's hand. The cold air box includes a test section inserting unit through which the test section of the patient's hand is inserted into a positioning unit. The positioning unit properly positions the test section within a visual field of the radiation thermometer. A fan blows cold air to the positioned test section, thereby allowing simple and accurate measuring of the skin temperature, while avoiding unnecesary pain to the patient.

3 Claims, 5 Drawing Sheets

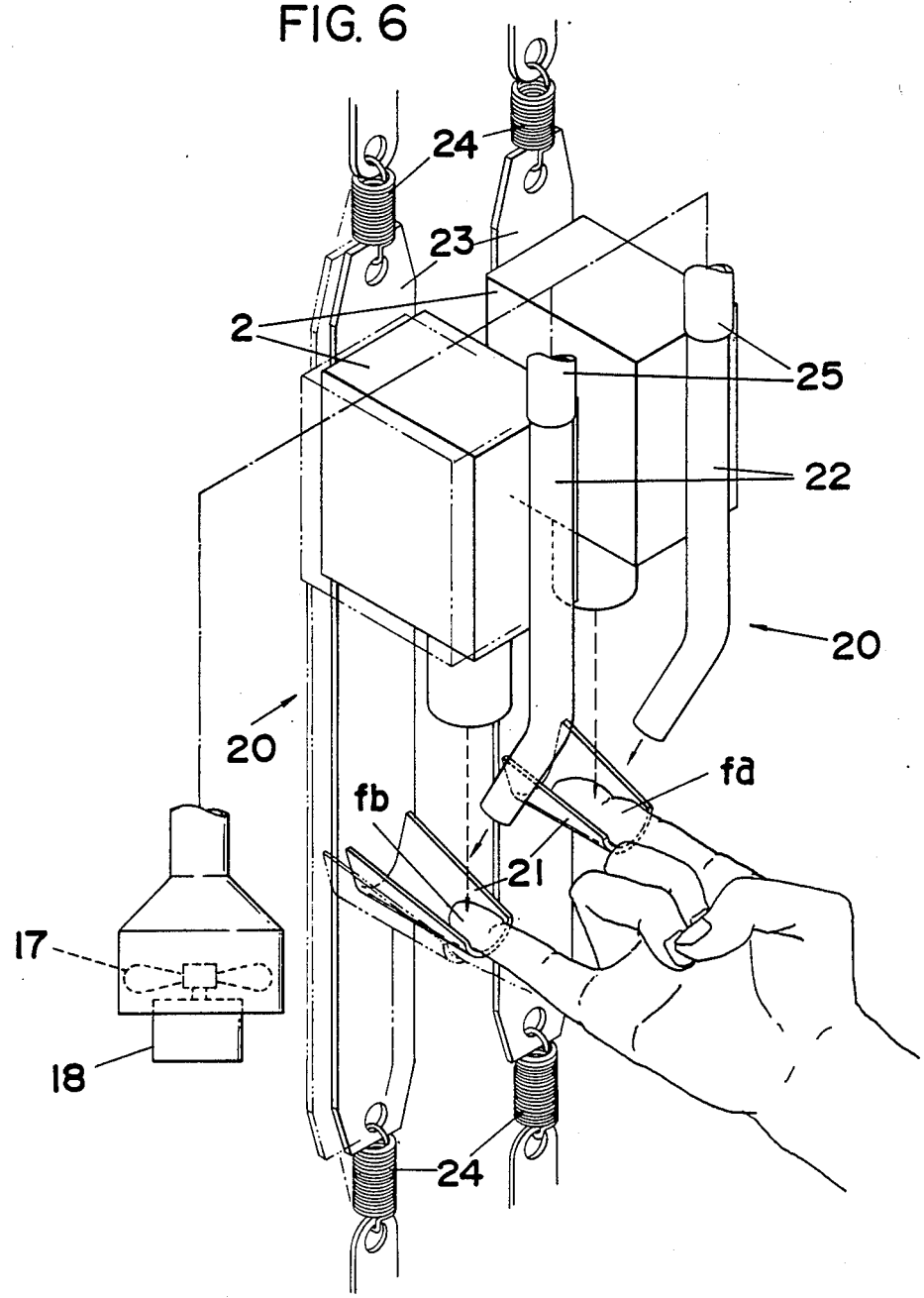

SKIN TEMPERATURE MEASURING APPARATUS FOR DIAGNOSING DISTURBANCE OF PERIPHERAL CIRCULATION

BACKGROUND OF THE INVENTION

1. Field of the Invention

This invention relates to a skin temperature measuring apparatus for diagnosing disturbance of a peripheral circulation and, more particularly, to an apparatus for measuring skin temperature by a radiation thermometer while blowing cold air to the skin.

2. Description of the Prior Art:

It has been known that, when a worker suffers from a vibration disease, a diffuse collagen disease or a diabetes mellitus, he has disturbance of peripheral circulation. When he suffers from the disturbance of the peripheral circulation, disturbance of blood stream occurs in his peripheral circulation system such as his fingers, and he exhibits abnormal skin temperature as the disturbance of the blood stream. Thus, it is effective to measure the skin temperature such as at his fingers as a method for diagnosing the disturbance of the peripheral circulation.

As means for measuring skin temperature of fingers, a method for measuring skin temperature is by, for example, the apparatus as shown in FIG. 7(a). A thermocouple 52 is attached to a finger by an adhesive tape 51 while dipping the finger in cold water 53 (generally at 5° C.) for a predetermined time (generally for 10 min.) to measure the skin temperature during this period. The finger is then removed from the cold water 53. The skin temperature is continuously measured for a predetermined time (generally for 10 min.) in the air as shown in FIG. 7(b). This procedure has been heretofore known. However, this method had the following drawbacks.

(i) A third party, such as a nurse, must attach the thermocouple by adhesive tape to the person's finger to be measured. In this case, the thermocouple must be tightly and correctly attached to the finger. If the attachment of the thermocouple to the finger is wrong, a large error is generated at the measured value.

(ii) When the finger is immersed in the cold water for a long period of time, the person or worker with the disturbance of the peripheral circulation suffers from large pains. When the fingers are dipped in the cold water, the patient's blood pressure rises. Thus, this procedure is very dangerous for the person with hypertension, heart failure or an aged person.

(iii) When the skin temperature is measured in the air after the temperature has been measured in the cold water, a large measuring error is generated due to external factors such as the degree of the atmospheric air temperature and the presence or absence, or the degree of wind or air flow. If the finger is moved during the measurement, a large measuring error occurs due to the air or wind created by movement.

As described above, the conventional method for measuring the skin temperature has a number of serious drawbacks. Therefore, the conventional method has not been frequently carried out as a method for dispensing the disturbance of the peripheral circulation.

SUMMARY OF THE INVENTION

An object of this invention is to provide a skin temperature measuring apparatus for diagnosing disturbance of peripheral circulation capable of simply and accurately measuring skin temperature, without pains to the person to be measured.

This invention does not measure the skin temperature by dipping a finger in cold water as in the conventional method, but measures the skin temperature in a cold air box with a thermo regulator, avoiding pain to the patients. As a skin temperature measuring instrument, a radiation thermometer is employed instead of a thermocouple to measure the skin temperature without contacting the skin. In order to prevent the measuring error due to the stay of the atmospheric air, a fan blows cold air to a test section of the skin during the temperature measurement to accurately measure the skin temperature.

Further, the skin temperatures of not only the test section but also a reference section are simultaneously measured, and the two measured results are compared, thereby more accurately diagnosing the disturbance of the peripheral circulation. Therefore, this invention provides positioning units at both the test section and the reference section in a cold air box having a thermo regulator to simultaneously measure the skin temperatures of both the test section and the reference section by two radiation thermometers. According to this invention, the above-mentioned drawbacks of the conventional one can be eliminated, and the measurement of the skin temperature necessary to diagnose the disturbance of the peripheral circulation can be accurately executed without pain to the person's fingers to be measured.

BRIEF DESCRIPTION OF THE DRAWINGS

FIG. 6 is a perspective view of the arrangement of a third embodiment apparatus according to the invention.

DESCRIPTION OF THE PREFERRED EMBODIMENTS

Embodiments of this invention will be described in detail with reference to the accompanying drawings.

Figure 1:
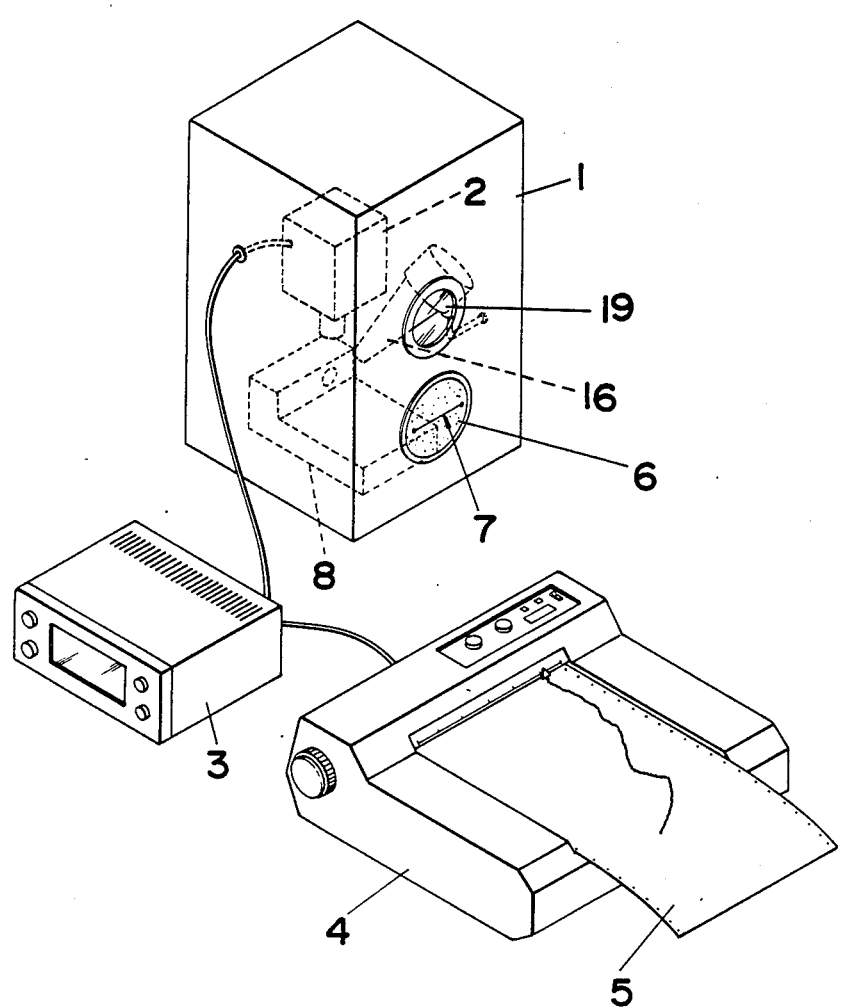
FIG. 1 is a perspective view of an embodiment of a skin temperature measuring apparatus for diagnosing disturbance of peripheral circulation according to this invention.
Figure 2:
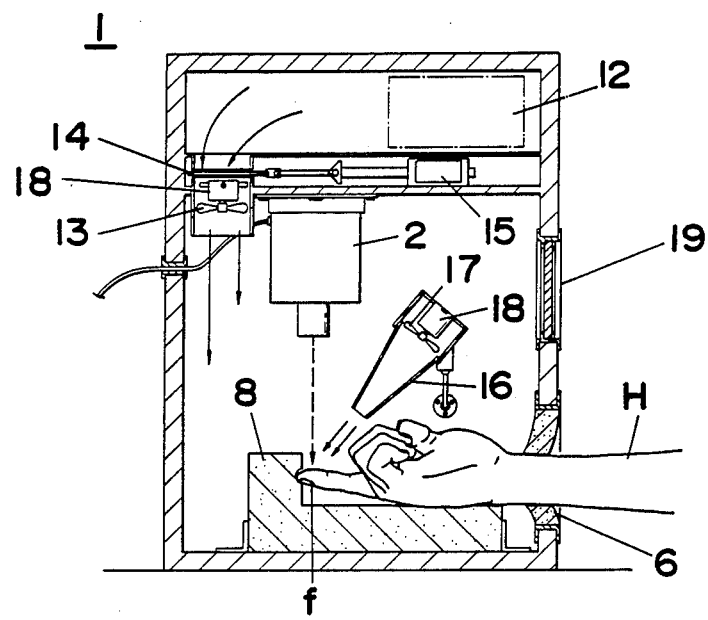
FIG. 2 is a sectional view of the embodiment of the invention.

In FIGS. 1 and 2, which show an embodiment of a skin temperature measuring apparatus according to this invention, the apparatus comprises a cold air box 1 with thermo regulator, radiation thermometers 2 are provided in the cold air box 1. A a thermo transmitter 3 connects radiation thermometers 2 to a recorder 4 receiving a recording sheet 5.

Figure 3:
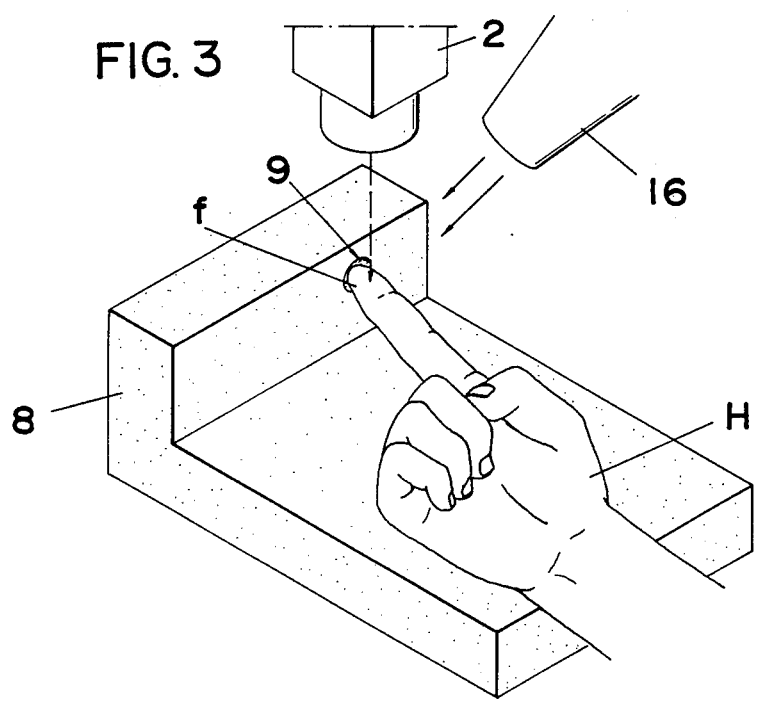
FIG. 3 is a perspective view of positioning unit of the apparatus.

The apparatus also comprises an inserting unit 6 of a hand H, provided on the side wall of the cold air tank 1. Inserting unit 6 is formed of a soft sponge plate. The inserting unit 6 has a slit 7 formed at the center thereof for freely inserting or removing the hand H into or from the apparatus. The sponge plate 6 holds the airtightness of the cold air tank 1 in close contact with the arm of the hand when hand H is inserted into the apparatus. The apparatus also comprises a positioning unit 8 for properly placing fingers f in the cold air tank 1. The positioning unit 8 has a positioning portion 9 for finger f in a circular groove shape on the front wall thereof (FIG. 3). The patient's hand H is placed on the positioning unit 8, and the finger is inserted into the positioning portion 9 to thereby position the finger f in the visual field of the radiation thermometer 2. The positioning unit 8 is formed of a soft material such as sponge or rubber for a person to be measured so as not to suffer from pains at his hand H. The apparatus also comprises a window 19 for observing the interior of the cold air tank 1 with the thermo regulator.

The thermo regulator of the apparatus comprises a refrigerating machine 12 provided in the upper portion of the cold air tank 1, a fan 13, an openable damper 14, and a solenoid 15 for opening the damper 14 feed cold air by the fan 13 into the cold air tank 1. The cold air tank 1 with the thermo regulator is set to an arbitrary temperature in a range of 0° C. to 7° C. In other words, if the cold air tank 1 is set to the temperature as low as 0° C., the physical pains of the person to be measured increased to become a drawback. If the cold air tank 1 is set to the temperature as high as 7° C., it is excessively warmer. Thus, the temperature of the range of 0° C. to 7° C. is preferable, and the temperature of the cold air tank 1 is more desirably in a range of 4° C. to 7° C. A nozzle 16 is provided to blow the cold air by a fan 17 to the finger f. When the cold air is thus blown to the finger f, it can prevent the cold air from staying on the surface of the finger 1 causing error to occur in the measurement of the skin temperature. Fan 17 is operated by a motor 18.

The skin temperature measuring apparatus of the invention is constructed as described above, and a method for measuring the skin temperature of the finger 1 will be described.

The hand H is first inserted into the cold air tank 1 with the thermo regulator of low temperature. This cold air tank 1 is maintained at low temperature (5° C. in this embodiment), by thermo regulator 12, 13, 14, 15. The drop of the skin temperature is measured by the radiation thermometer 2. In this case, the fan 17 is driven to blow the cold air from the nozzle 16 to the finger f to prevent the air from staying in the vicinity of the finger f. Before measuring the skin temperature in the cold air tank 1 with the thermo regulator, it is preferable to maintain the initial conditions constant such as by standing by the person to be measured for a predetermined time (e.g., 15 min.) in a room which is held at a predetermined temperature (e.g., 25° C.), providing a cold air tank of high temperature (e.g., 25° C.) or inserting the hand for a predetermined time (e.g., 15 min.) in the cold air tank 1 with the thermo regulator.

Figure 4:
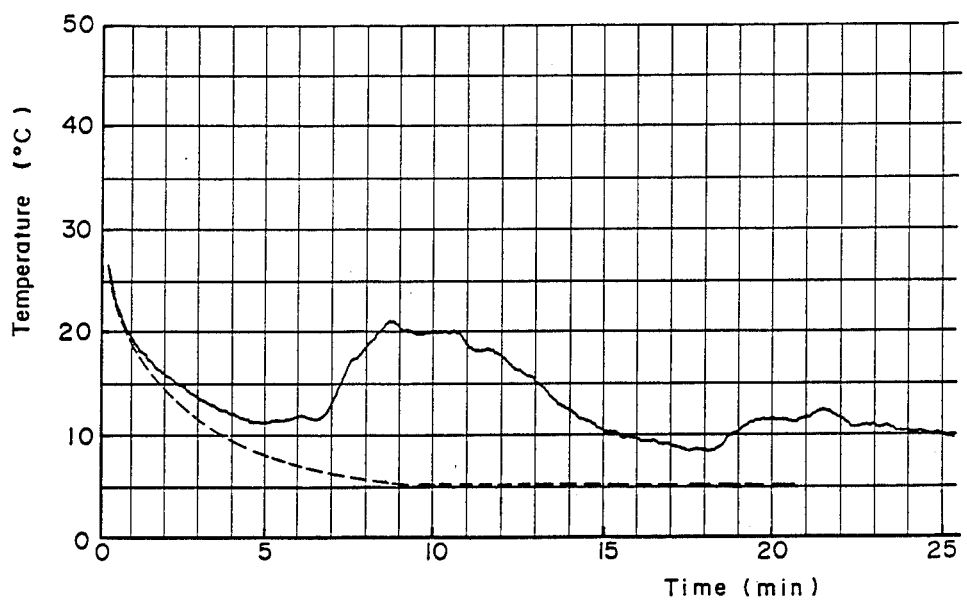
FIG. 4 is a graph showing the relationship between the temperature and the time.

FIG. 4 shows a temperature curve of the case that the hand H is inserted into the cold air tank 1 with the thermo regulator held at 5° C. as described above, wherein a solid line indicates the curve of a healthy subject and a broken line indicates the curve of a worker with disturbance of peripheral circulation. In the case of the healthy subject, the skin temperature slowly falls as the finger f is cooled, falls to the vicinity of 10° C. after 5 min, but reversely rises after 7 min, and recovers up to 21° C. after 8 min. and 40 sec. However, the skin temperature of the healthy subject again starts falling, and falls up to 8° C. after 18 min. Then, the skin temperature of the healthy subject again reversely rises, and rises up to 12° C. after 20 min. After 22 min. the skin temperature of the healthy subject again starts falling. In this manner, even if the skin temperature of the healthy subject drops to a predetermined temperature, it again rises to a predetermined temperature by the cold-induced vasodilatation of the peripheral circulation system. This point is remarkable difference from the case of the worker with the disturbance of the peripheral circulation to be described next. In case of the worker with the disturbance of the peripheral circulation, as is apparent from the broken line curve in FIG. 4, the skin temperature of the worker with the disturbance of the peripheral circulation abruptly drops simultaneously when the hand H of the worker with the disturbance of the peripheral circulation is inserted into the cold air tank 1 with the thermo regulator, and drops up to the vicinity of the room temperature (5° C.) of the cold air tank 1 with the thermo regulator after 10 min. In the case of the worker with the disturbance of the peripheral circulation, the cold-induced vasodilatation of the healthy subject is not observed, and the skin temperature which has once fallen no longer rises. In this manner, according to the method for measuring the skin temperature, the healthy subject and the worker with the disturbance of the peripheral circulation can be distinctly distinguished by the presence or absence of the cold-induced vasodilatation. When the skin temperature is measured in the cold air tank 1 with the thermo regulator of low temperature, the skin temperature may be measured while applying a vibration load to the finger f by vibrating the positioning unit 8 by a vibrating unit (not shown).

Figure 5:
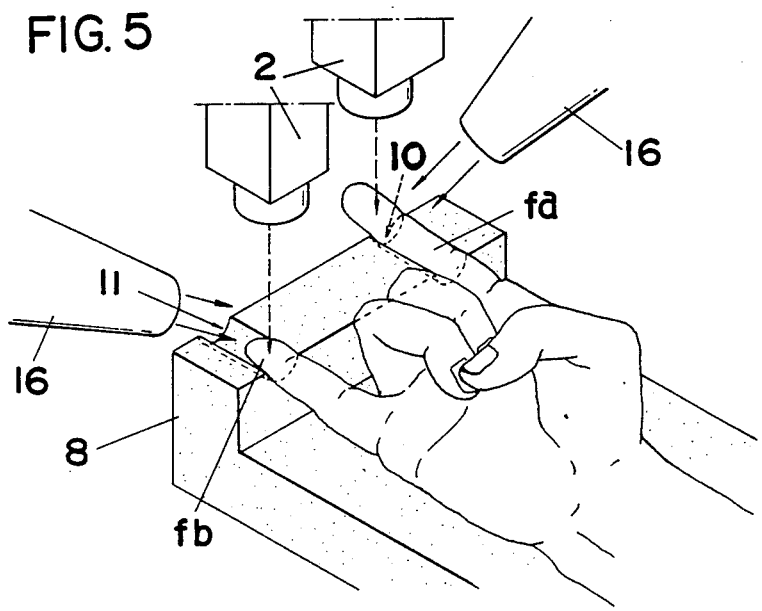
FIG. 5 is a perspective view of a second embodiment of the apparatus according to this invention.
Figure 7A:
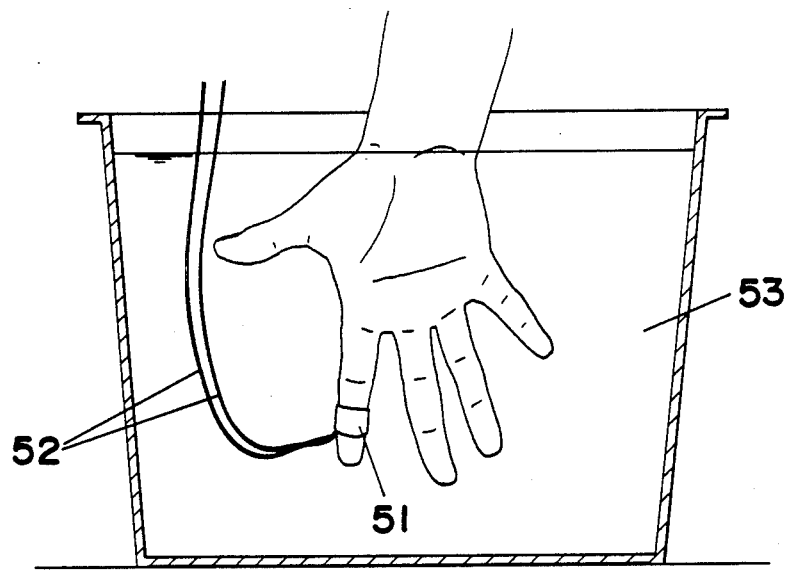
FIGS. 7(a) and 7(b) are front views of the conventional apparatus.
Figure 7B:
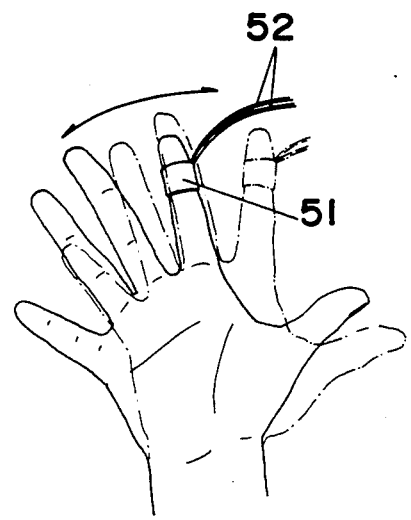

In FIG. 5, showing a second embodiment of this invention, a cold air tank 1 with thermo regulator has two radiation thermometers 2, 2, and two positioning portions 10, 11 formed in groove shapes on the positioning unit 8. One positioning portion 10 positions the second finger fa which feasibly suffers from disturbance of peripheral circulation, and the other positioning portion 11 positions the little or fifth finger fb which hardly suffers from disturbance of peripheral circulation. In this case, nozzles 16 and fans 17 are provided to blow cold air to the fingers fa and fb. When the skin temperatures of the finger fa of the test section and the finger fb of the reference section are simultaneously measured in this manner, the presence or absence and the degree of the disturbance of the peripheral circulation of the second finger fa can be more accurately diagnosed by comparing the two results.

In FIG. 6, which shows a third embodiment of this invention, radiation thermometers 2, 2, positioning units 21, 21 and nozzles 22, 22 are integrally mounted on plates 23, 23, respectively to construct measuring units 20, 20. Each plate 23 is supported at the upper and lower surfaces by springs 24, 24 about which measuring units 20, 20 are pivotable. Thus, the positioning units 21, 21 can be freely displaced (as designated by broken lines) according to the size of the hand and the lengths of the fingers, and even if displaced, the fingers fa, fb can be maintained within the visual field of the radiation thermometers 2, 2. This embodiment also comprises tubes 25 for blowing cold airs by a fan 17 to the fingers fa, fb.

According to this invention as described above, the skin temperature or temperatures are measured by the cold air tank with the thermo regulator or low temperature. Therefore, the pains of the person to be measured are much less than the conventional means for measuring the skin temperature in cold water, and the skin temperature can be accurately measured irrespective of the external factors. Since this invention measures the skin temperatures in non-contact by the radiation thermometer while blowing the cold air by the fan, the skin temperature can be remarkably accurately measured.

What is claimed is:

1. A skin temperature measuring apparatus for a test section of a patient's skin, the apparatus comprising:
    a cold air box having a thermo regulator of low temperature;
    a radiation thermometer means for measuring the skin temperature of a test section of the patient's skin disclosed in said cold air box and having a visual field extending through said cold air box;
    said cold air box comprising a test section inserting unit, a positioning unit adapted to receive the inserted test section within the visual field of said radiation thermometer, means and a fan for blowing cold air to the positioned test section.

2. The skin temperature measuring apparatus according to claim 1 wherein measurement is taken with respect to a reference section, wherein said cold air box further comprises a second radiation thermometer means for measuring the skin temperature of a reference section of the patient's skin, having a visual field, and a second positioning unit adapted to receive the reference section within the visual field of said two radiation thermometer means, and a fan for blowing cold air to the positioned test section and reference section.

3. The skin temperature measuring apparatus according to claim 1, wherein said radiation thermometer means and said positioning unit form an integral measuring unit, and wherein said measuring unit is pivotable with respect to said cold air box.

* * * * *